(12) United States Patent
Chung et al.

(10) Patent No.: US 8,911,605 B2
(45) Date of Patent: Dec. 16, 2014

(54) METHOD FOR ANTIBIOTIC SUSCEPTIBILITY TESTING AND DETERMINING MINIMUM INHIBITORY CONCENTRATION OF THE ANTIBIOTIC

(75) Inventors: Cheng-Che Chung, Tainan (TW);
I-Fang Cheng, Tainan (TW);
Wen-Horng Yang, Tainan (TW);
Hsien-Chang Chang, Tainan (TW)

(73) Assignee: National Cheng Kung University, Tainan (TW)

( * ) Notice: Subject to any disclaimer, the term of this patent is extended or adjusted under 35 U.S.C. 154(b) by 269 days.

(21) Appl. No.: 13/473,717

(22) Filed: May 17, 2012

(65) Prior Publication Data

US 2013/0008793 A1    Jan. 10, 2013

(30) Foreign Application Priority Data

Jul. 5, 2011    (TW) .............................. 100123735 A

(51) Int. Cl.
*G01N 27/447*    (2006.01)
*G01N 33/15*    (2006.01)
*C12Q 1/18*    (2006.01)

(52) U.S. Cl.
CPC . *G01N 33/15* (2013.01); *C12Q 1/18* (2013.01)
USPC ........................................................ 204/547

(58) Field of Classification Search
CPC ............................................... B03C 5/00–5/28
See application file for complete search history.

(56) References Cited

FOREIGN PATENT DOCUMENTS

TW    I245900 B    12/2005

OTHER PUBLICATIONS

Johari et al. "Dielectrophoretic assay of bacterial resistance to antibiotics," Phys. Med. Biol. 48 (2003) N193-N198.*
Hoettges et al. "Dielectrophoresis-Activated Multiwell Plate for Label-Free High-Throughput Drug Assessment," Anal. Chem. 2008, 80, 2063-2068.*
Fomchenkov et al. "A study of the effect of antibiotics on orientational and dielectrophoretic spectra of bacterial cells," Journal of Biological Physics (1979), 7, 45-56.*
Belgian Biosafety Server—Antibioresistance Archive—Aminoglycoside resistance entry, downloaded from http://www.antibioresistance.be/aminoglycosides.html on May 5, 2014.*
University of Rochester Medical Center Research Network entry for *Staphylococcus epidermidis* downloaded from http://www.urmc.rochester.edu/profiles/display/115701 on May 5, 2014.*
Jennifer Andrews, "Determination of minimum inhibitory concentrations," Journal of Antimicrobial Chemotherapy (2001) 48, Suppl. S1, 5-16.*

(Continued)

*Primary Examiner* — Alex Noguerola
(74) *Attorney, Agent, or Firm* — Bacon & Thomas, PLLC

(57) ABSTRACT

A method of antibiotic susceptibility testing is disclosed, and includes the following steps: (A) providing a sample to be tested wherein the sample contains a microbe; (B) adding an antibiotic into the sample, wherein the antibiotic serves to inhibit cell wall synthesis; (C) checking the sample by dielectrophoresis and observing a shape change of the microbe; and (D) determining whether the microbe is susceptible to the antibiotic according to the shape change thereof. The present invention also discloses a method for determining a minimum inhibitory concentration of the antibiotic.

8 Claims, 8 Drawing Sheets

(56) References Cited

OTHER PUBLICATIONS

Chung et al., "Antibiotic susceptibility test based on the dielectrophoretic behavior of elongated *Escherichia coli* with cephalexin treatment", Biomicrofluidics, 2011, vol. 5, pp. 021102-1 to 021102-6.

Hoettges et al., "Rapid determination of antibiotic resistance in *E. coli* using dielectrophoresis", Physics in Medicine and Biology, 2007, vol. 52, pp. 6001-6009.

Hsien-Chang Chang et al., Biochip development for rapid screening for urinary tract infection and antibiotic selection, May 17, 2011, p. 103-111, Taiwan R.O.C.

* cited by examiner

METHOD FOR ANTIBIOTIC SUSCEPTIBILITY TESTING AND DETERMINING MINIMUM INHIBITORY CONCENTRATION OF THE ANTIBIOTIC

CROSS REFERENCE TO RELATED APPLICATION

This application claims the benefits of the Taiwan Patent Application Serial Number 100123735, filed on Nov. 17, 2011, the subject matter of which is incorporated herein by reference.

BACKGROUND OF THE INVENTION

1. Field of the Invention

The present invention relates to a method of antibiotic susceptibility testing and for determining a minimum inhibitory concentration of the antibiotic and, more particularly, to a method of antibiotic susceptibility testing and for determining a minimum inhibitory concentration of the antibiotic, which both employ dielectrophoresis and the antibiotic inhibiting cell wall synthesis to detect rod-shaped microbes.

2. Description of Related Art

Currently, clinically assessing effects of an antibiotic on pathogenic bacteria is generally achieved by an in vitro test which determines antibiotic susceptibility of the bacteria. There are many such in vitro tests, for example, a minimum inhibitory concentration (MIC) test, a disk-diffusion test, a checkerboard test, a minimum bactericidal concentration (MBC), a time-kill curves test, and so on. These tests can be used according to requirements such as timeliness and accuracy.

Among the tests listed above, the disk-diffusion test is a method that is most common and rapid because this method is simple and economical. However, after the method is executed, only qualitative information can be obtained, and thus this cannot serve as a basis for the regulation of antibiotic doses. Accordingly, if the regulation of antibiotic doses is required, an MIC test can be performed to afford quantitative information which is the basis for the use of antibiotics.

In the traditional MIC test, optical measurement is a common means. When microbes are treated with an antibiotic for 18-24 hours, optical density of the culture medium is measured by a spectrometer so as to determine whether microbial growth is inhibited or not. Accordingly, conventional optical measurement requires at least 18-24 hours for microbial growth. If a microbe grows very slowly, culturing the microbe needs even more time. Therefore, if timeliness is required, for example, diagnosing acute microbial infections such as bacteremia and meningitis, conventional optical measurement is often too slow to resolve critical situations. Hence, meeting clinical emergencies is difficult via conventional optical measurements.

Since conventional methods generally consume several days and are unable to provide timely final results, there is an urgent need to develop a technique for rapidly determining antibiotic susceptibility and a MIC of the antibiotic. The technique of the present invention is able to check whether microbes have antibiotic resistance within 1-2 hours and to afford an antibiotic MIC so as to meet clinical requirements and benefit the public.

SUMMARY OF THE INVENTION

The object of the present invention is to provide a method of antibiotic susceptibility testing. In this method, because microbes have different dielectrophoretic behavior in different media, dielectrophoresis is carried out in the presence of a specific antibiotic that inhibits cell wall synthesis, and under a non-uniform electric field of alternating current so that drug-resistant microbes can be identified according to the elongation of these microbes.

In order to achieve the object described above, one aspect of the present invention provides a method of antibiotic susceptibility testing, comprising the following steps: (A) providing a test sample containing a microbe; (B) adding an antibiotic to the test sample, wherein the antibiotic is used to inhibit cell wall synthesis; (C) executing dielectrophoresis to the test sample and observing morphologic changes of the microbe in the test sample; and (D) determining whether the microbe is resistant to the antibiotic according to the morphologic changes of the microbe.

In the method of the present invention, when the microbe is actually inhibited by the aforesaid antibiotic, morphological changes of the microbe occur due to cell wall changes of the microbe, resulting in changes in dielectrophoretic property. Under an electric field, these changes can be recognized and thus the microbe can be identified as a microbe having no drug resistance to the antibiotic. Conversely, when the microbe is actually not inhibited by the aforesaid antibiotic, morphological changes of the microbe do not occur due to an intact cell wall of the microbe. Accordingly, an influence on dielectrophoretic property is not present during dielectrophoresis. Under an electric field, the changes in dielectrophoretic property are not recognized and thus the microbe can be identified as a microbe having drug resistance to the antibiotic.

Another object of the present invention is to provide a method for determining a minimum inhibitory concentration of an antibiotic. In the method, because microbes have different dielectrophoretic behavior in different media, dielectrophoresis is carried out in the presence of a specific antibiotic that inhibits cell wall synthesis and under a non-uniform electric field of alternating current so that a minimum inhibitory concentration (MIC) of the antibiotic can be determined according to elongation and crossover frequency changes of these microbes. Therefore, the MIC can be a basis for the clinical regulation of doses.

In order to achieve the above object, another aspect of the present invention provides a method for determining a minimum inhibitory concentration of an antibiotic, comprising the following steps: (A) providing a test sample containing a microbe; (B) adding an antibiotic with different concentrations to the test sample, wherein the antibiotic is used to inhibit cell wall synthesis; (C) executing dielectrophoresis to the test sample and observing morphologic changes and crossover frequency changes of the microbe in the test sample; and (D) determining the minimum inhibitory concentration of the antibiotic according to the morphologic changes and the crossover frequency changes of the microbe.

In the aforesaid method of the present invention, when the concentration of the antibiotic reaches the MIC, elongation of the microbe occurs significantly and a decrease in crossover frequency reaches a maximum. Conversely, when the concentration of the antibiotic does not yet reach the MIC, it is difficult to find elongation of the microbe and the decrease in crossover frequency does not reach a maximum.

In the method of the present invention, microbes that can be tested are mainly rod-shaped bacteria. Because rod-shaped bacteria have major and minor axes, it is difficult for the bacteria, of which the cell wall is influenced by the antibiotic, to keep their original shape. Under an electric field during dielectrophoresis, because forces exerted to major and minor axes of the bacteria are different and the ability of the cell wall to stabilize bacterial shapes is reduced, elongation of the rod-shaped bacteria can be found. In an example of the present invention, the microbe is a Gram-negative rod-shaped bacterium, for example, *Escherichia coli, Proteusbacillus vulgaris, Klebsiella pneumoniae*, and *Pseudomonas aeruginosa*.

In the method of the present invention, the antibiotic is used to affect the cell wall of the microbe and to weaken the structural strength of the cell wall, which then makes the microbe not keep its original morphology. Hence, in the present invention, morphological changes of the microbe during dielectrophoresis are the basis to determine whether the microbe is inhibited by the antibiotic. In an example of the present invention, the antibiotic is a β-lactam antibiotic, for example, cephalosporins, monobactams, penicillins, carbapenems, and a combination thereof. For the aforesaid purpose of reducing structural strength of microbial cell walls, these antibiotics function as an inhibitor of cell wall synthesis.

In step (B) of the aforesaid method according to the present invention, the antibiotic is present in the test sample for a predetermined period of time, and the predetermined period of time can be 60-120 minutes.

In an example of the present invention, a β-lactam antibiotic acts on Enterobacteriaceae for antibiotic susceptibility testing. The microbe is incubated in a broth containing the antibiotic for 1-2 hours and then a little of the microbial suspension is taken out on a chip for dielectrophoretic testing. In addition, in order to minimize the personal equation in operation, the technique of the present invention will be combined with microfluidic techniques in the fixture. In other words, incubation of the microbe for 1-2 hours is integrated with a microfluidic chip and thus the chip can be used for susceptibility testing of various drugs at the same time. Alternatively, a two-dimensional microelectrode array chip established by microelectromechanical techniques is integrated with a microelectric signal supply and an optical module to form a miniaturized chip system. Therefore, as compared with a common large-scaled apparatus having similar functions, the miniaturized chip system is inexpensive and extremely suitable for various inspection departments of any scale level.

In general, bacteria change membrane permeability and antibiotic binding domains and secrete enzymes that decompose an antibiotic so as to resist the antibiotic. Once bacteria possess drug resistance, elongation of the bacteria cannot be induced by the drug.

Accordingly, elongation of bacteria is the basis to determine whether the bacteria have drug resistance, and thus the duration of the method of the present invention is about 1-2 hours. Compared with a conventional disk-diffusion test and a dilution method which need 18-24 hours for bacterial growth, the present invention has considerably reduced the duration of inspection and simultaneously can determine a MIC and whether bacteria have drug resistance.

In conclusion, compared with conventional clinical antibiotic susceptibility testing that requires 18-24 hours, the method of the present invention can determine a MIC and whether a microbe has drug resistance within 1-2 hours. Therefore, the duration of testing can be considerably reduced. The method of the present invention can be used as a guideline of drug use in clinical medicine and as a standard of antibiotic dose added to livestock feed in pasturage or fishery so as to reduce the probability that pathogens have drug resistance.

Other objects, advantages, and novel features of the invention will become more apparent from the following detailed description when taken in conjunction with the accompanying drawings.

DETAILED DESCRIPTION OF THE PREFERRED EMBODIMENT

Figure 1:
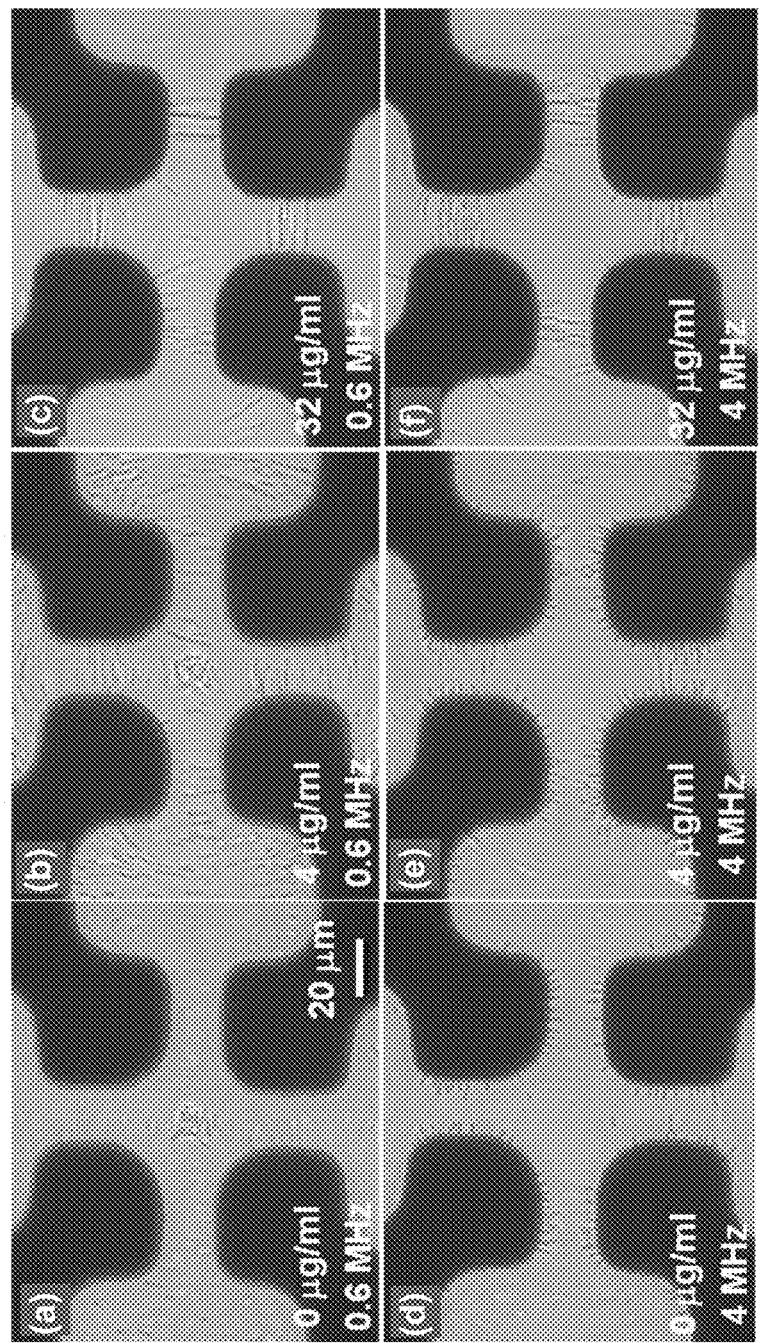
FIG. 1 shows microscopic photographs of a dielectrophoretic test in Example 1 of the present invention, wherein (a) to (c) respectively show test results at antibiotic concentrations of 0 μg/ml, 4 μg/ml and 32 μg/ml under 600 kHz, and (d) to (f) respectively show test results at antibiotic concentrations of 0 μg/ml, 4 μg/ml and 32 μg/ml under 4 MHz.

Antibiotics for inhibiting cell wall synthesis, for example β-lactam antibiotics, are used to act on rod-shaped bacteria, for example Gram-negative rod-shaped bacteria, in the present invention. In addition, microbes treated with the antibiotics are analyzed by dielectrophoresis and observed regarding changes in crossover frequency and morphology during dielectrophoresis. Accordingly, determination of the minimum inhibitory concentration (MIC) and whether the microbes are resistant to the antibiotics can be rapidly accomplished.

β-Lactam antibiotics include penicillins, cepholasporins, monobactams, and carbapenems and they act on the inhibition of cell wall synthesis. In general, microbes treated with such antibiotics at a relatively low concentration suffer cell elongation, but they lyse if treated at a higher concentration.

In conventional methods, determining whether cell walls are damaged or perforated and whether cytoplasm in microbes leaks out can achieve clear differentiation between live and dead microbes. Similarly, during dielectrophoresis, dielectrophoretic properties of microbes are changed due to different conductivities when the microbes transform from live to dead cells. Accordingly, determining whether microbes are live can be realized by dielectrophoresis. In addition, dielectrophoretic properties are also changed due to microbial morphological changes. Generally, charges induced by an electrical field are more at both ends of longer thin microbes than those at the central surface thereof, and similarly, induced dipole moments are also larger at both ends than those at the central surface. Thus, positive dielectrophoretic force can be more easily induced at relatively low frequency.

Accordingly, the present invention employs enterobacteria, for example *E. coli* and *Klebsiella pneumoniae*, as a major test sample and cephalosporins such as cephalexin and cefazolin as test antibiotics. After such antibiotics act on microbes, morphological changes occur in microbes due to compositional changes in cell walls so that induced dielectrophoretic properties are changed. Therefore, changes in morphological elongation and crossover frequency can be used to determine the MIC of an antibiotic and whether microbes are resistant to the antibiotic. Notably, conventional serial dilution method is used as a control for antibiotic susceptibility testing (AST) in the present invention in order to ensure that the accuracy of the present invention is the same as or better than that of conventional methods.

Because of the specific embodiments illustrating the practice of the present invention, one skilled in the art can easily understand other advantages and efficiency of the present invention through the content disclosed therein. The present invention can also be practiced or applied by other variant embodiments. Many other possible modifications and variations of any detail in the present specification based on different outlooks and applications can be made without departing from the spirit of the invention.

The drawings of the embodiments in the present invention are all simplified charts or views, and only reveal elements relative to the present invention. The elements revealed in the drawings are not necessarily aspects of the practice, and quantity and shape thereof are optionally designed. Further, the design aspect of the elements can be more complex.

Preparation Example 1

Glass slides were used as substrates. Metal films were deposited on the glass slides by physical vapor deposition (PVD). In detail, Cr (50 nm) as an adhesive layer and then Au (200 nm) as a conductive layer were deposited on a glass slide by E-beam VT1-10CE (ULVAC).

After deposition of the metal films, a photoresist layer was formed on the metal films by standard photolithography, exposed with a mask having a predetermined pattern, and then developed to form the predetermined pattern. Subsequently, the pattern of the photoresist was transferred to the metal films by wet etching and then the photoresist was removed. Finally, patterned metal films were made to serve as a microelectrode array of a chip. Hence, the chip was obtained. In the chip, microelectrodes were separated by a distance of 20 μm and made in a width of 50 μm.

Preparation Example 2

The present example was the same as the manner of Preparation Example 1 except that the microelectrodes were made of transparent Indium tin oxide (ITO).

Example 1

Phosphate-buffered saline (PBS) containing 137 mM NaCl, 2.7 mM KCl, 4.3 mM $Na_2HPO_4$, and 1.47 mM $KH_2PO_4$ at pH 7.4 was prepared. An oral β-lactam antibiotic, cephalexin (Sigma, USA), which generally is used in the treatment of urinary tract infection (UTI), was dissolved in 1×PBS and prepared into a stock concentration of 1024 μg/mL. This stock concentration was diluted with trypticase soy broth (TBS) into 4 μg/mL and 32 μg/mL. Hence, TBS culture media with the antibiotic at different concentrations were made.

Among different cell lines of *Escherichia coli* causing urinary infection, *E. coli* ATCC 25922 was selected and cultured with TBS under shaking at 37° C. Then, the bacterial concentration of the culture suspensions was adjusted to $1.5 \times 10^6$ cells/ml by a densitometer (VITEK 2, BioMérieux).

The bacterial suspension (100 μl) and TBS culture media (containing the antibiotic at different concentrations, 900 μl) were mixed ($1.5 \times 10^6$ cells/ml) and incubated at 37° C. in a shaking incubator for 60 minutes. After the treatment, the bacterial suspensions (500-1000 μl) were centrifuged at 3000-5000 rpm for 3-5 minutes. The supernatant of the bacterial suspensions was removed. Finally, 0.2 M 4-(2-hydroxyethyl)-1-piperazineethanesulfonic acid (HEPES) buffer (500 μl, σ=3 mS/cm, Invitrogen 15630) was added to the remaining bacteria and the formed bacterial suspensions were shaken using a vortex mixer (Shin Kwang, Taiwan) for 30 seconds to avoid aggregation of the bacteria for the following dielectrophoretic tests.

The bacterial suspensions (5 μl) were pipetted into a sample well of the chip of Preparation Example 1. The electrode array was then connected to a function generator (Fluke 284 USA) and supplied with an alternating current signal or dielectrophoresis. The frequency of *E. coli* migrating from the electrode center to the electrode edge, was determined as crossover frequency (cof). During dielectrophoresis, the images were observed and recorded through an inverted microscope (Olympus IX70, Japan) and a CCD camera (Microfire, Optronics).

As shown in FIGS. 1 (*a*) to (*c*), at alternating current frequency of 600 kHz, bacteria on which the antibiotic does not act are arranged at the center of the electrodes by negative dielectrophoretic force. In the case of the antibiotic at 4 μg/ml, some bacteria are still arranged at the center of the electrodes by negative dielectrophoretic force. However, the others are adsorbed at the edges of the electrode by positive dielectrophoretic force and slightly elongated. In the case of being treated by the antibiotic at 32 μg/ml for 1 hour, all bacteria are adsorbed at the edges of the electrode by positive dielectrophoretic force and have become elongated. In addition, as shown in FIGS. 1 (*d*) to (*f*), at alternating current frequency of 4 MHz, bacteria on which the antibiotic does not act are arranged at the edges of the electrodes by positive dielectrophoretic force, and their cell elongation obviously does not occur. In the case of the antibiotic at 4 μg/ml, some bacteria are slightly elongated, and in the case of the antibiotic at 32 μg/ml for 1 hour, all bacteria have become elongated.

Example 2

In the same manner as that of Example 1, the antibiotic solutions at 1 μg/mL, 2 μg/mL, 4 μg/mL, 8 μg/mL, 16 μg/mL, 32 μg/mL, and 64 μg/mL were prepared and their action periods of time were 30, 60, and 120 minutes. In addition, the chip of Preparation Example 2 was used in the analysis. For measurement of the cell length of *E. coli* during dielectrophoresis, when the bacteria were straightly arranged on an ITO quadruple electrode by field-induced dielectrophoretic force, the cell length was analyzed by the image software (FreePlus32). The results are shown in FIGS. 2 and 3.

Figure 2A:
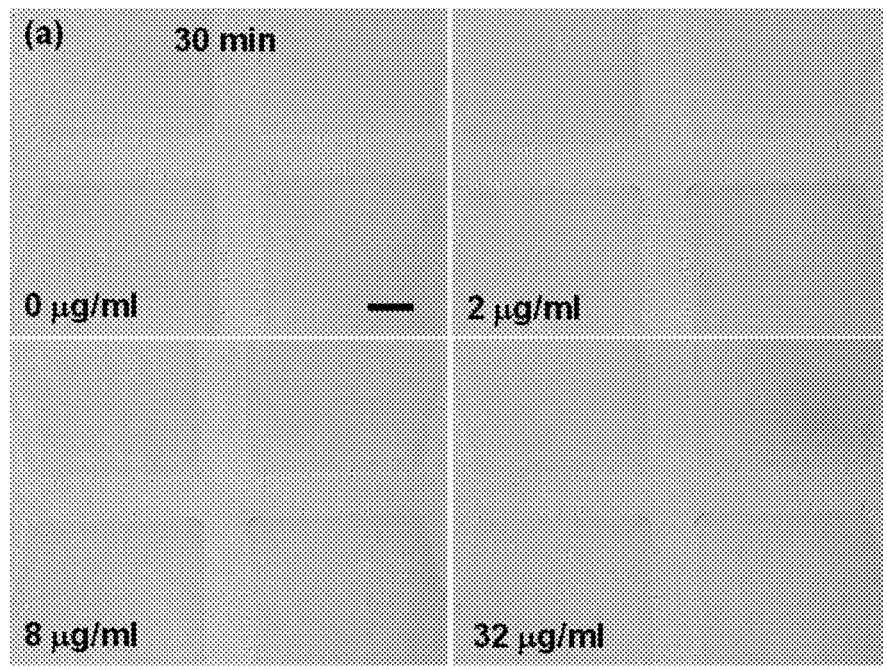
FIG. 2 shows microscopic photographs of a dielectrophoretic test in Example 2 of the present invention, wherein (a) shows test results at antibiotic concentrations of 0 μg/ml, 4 μg/ml, 8 μg/ml and 32 μg/ml for 30 minutes, (b) shows test results at antibiotic concentrations of 0 μg/ml, 4 μg/ml and 32 μg/ml for 60 minutes, and (c) shows test results at antibiotic concentrations of 0 μg/ml, 4 μg/ml, 8 μg/ml and 32 μg/ml for 120 minutes.
Figure 2B:
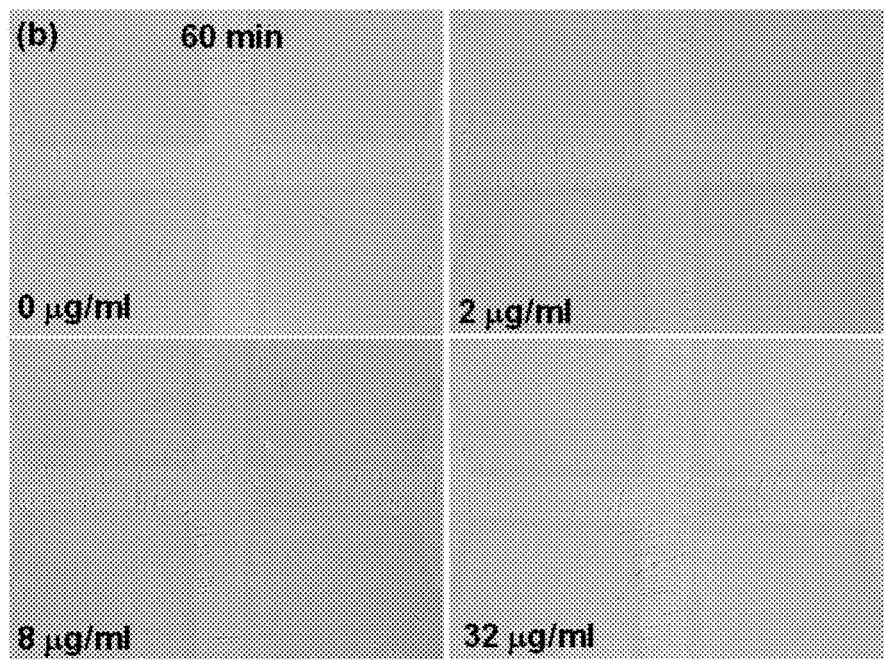
Figure 2C:
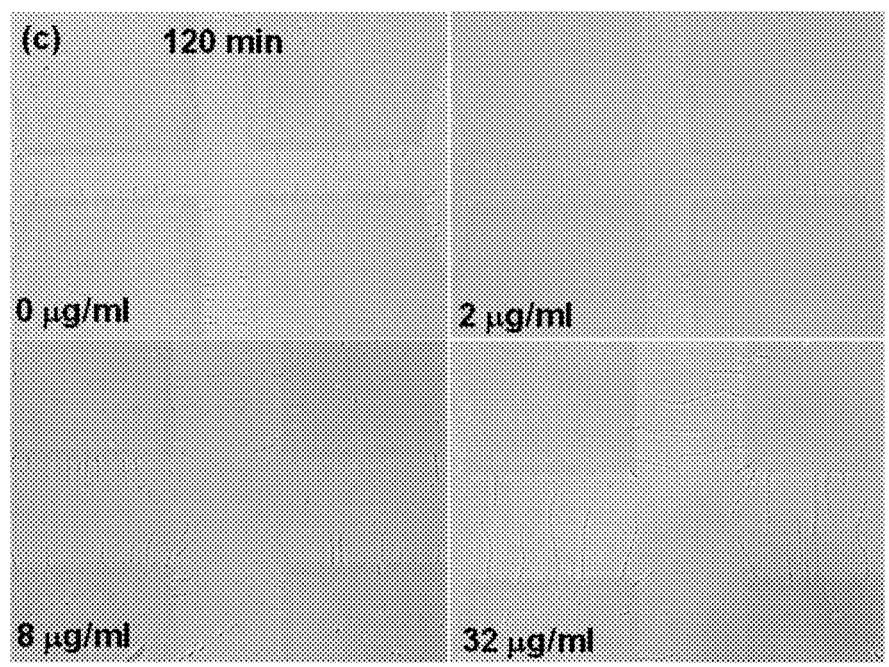

As shown in FIG. 2 (a), after antibiotic treatment for 30 minutes, distinction between morphological changes in bacteria is difficult. However, as shown in FIG. 2 (b), after antibiotic treatment for 60 minutes, morphological cell elongation occurs obviously as the antibiotic concentrations increase. Finally, as shown in FIG. 2 (c), subsequent to antibiotic treatment for 60 minutes, morphological cell elongation occurs obviously even at a low concentration of the antibiotic. This demonstrates that the antibiotic acts on the bacteria and cell elongation becomes obvious with an increase in the concentration of the antibiotic.

Figure 3A:
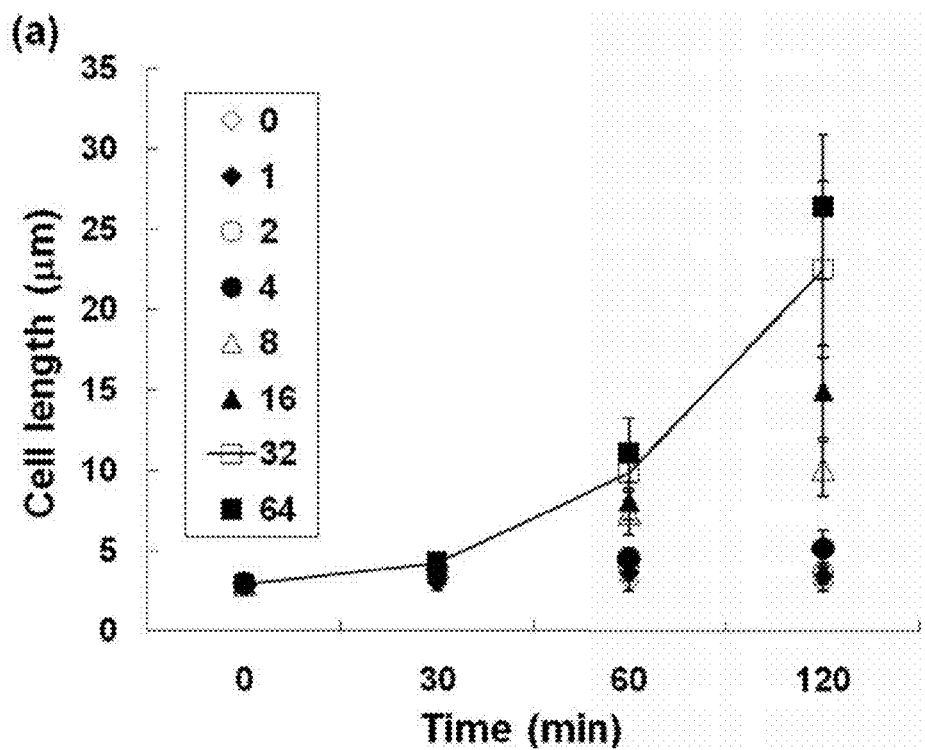
FIG. 3 shows relationships among cell length, antibiotic doses, reaction time, and crossover frequency of a dielectrophoretic test in Example 2 of the present invention, wherein (a) shows the relationship among cell length, antibiotic doses, and crossover frequency; (b) shows the relationship among antibiotic doses, reaction time, and crossover frequency, and (c) shows the relationship among cell length, antibiotic doses, and reaction time.
Figure 3B:
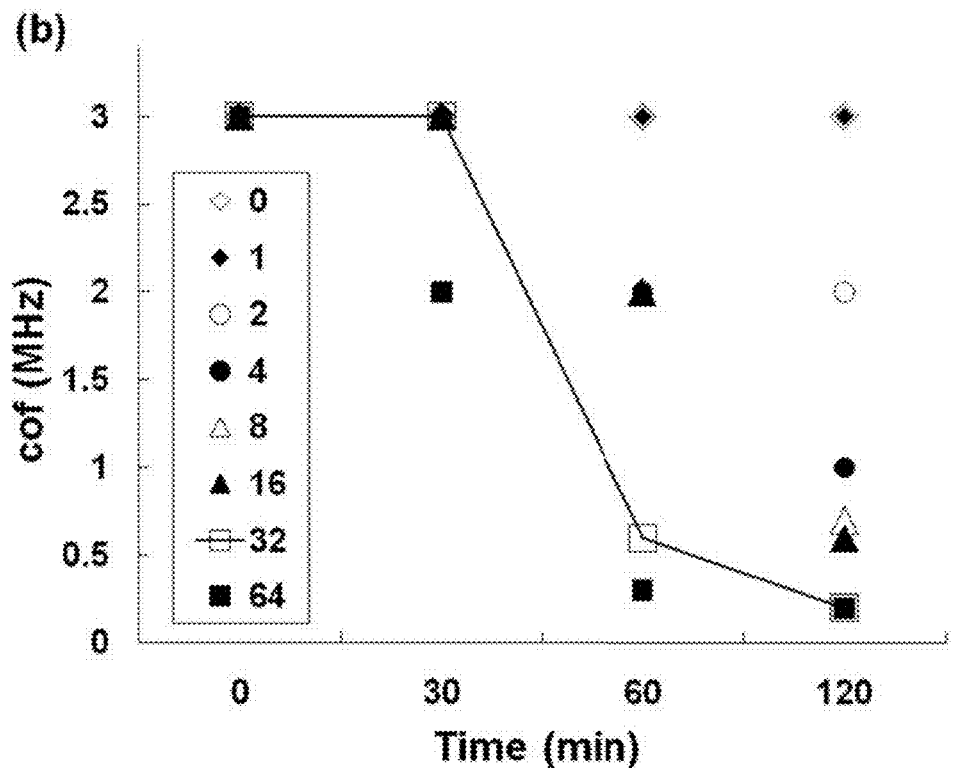
Figure 3C:
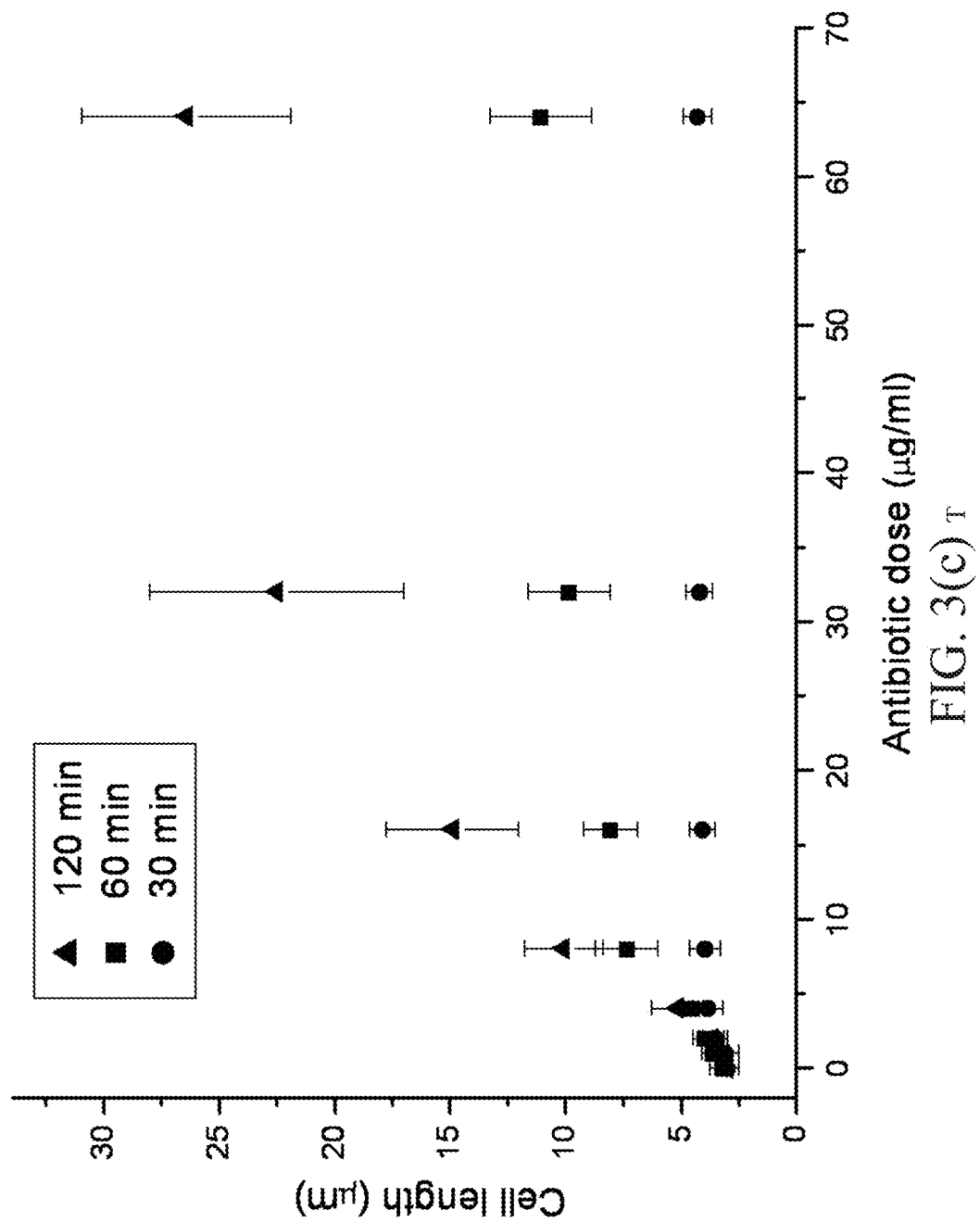

With reference to FIGS. 3 (a) and (c), they show relationships among the concentration and action time of the antibiotic and cell length. Based on these features, it can be understood that cell length increases as the concentration and action time increase. With reference to FIG. 3 (b), it shows a relationship among the concentration and action time of the antibiotic and crossover frequency (cof). Based on this feature, it can be known that the crossover frequency reduces to about 600 kHz after antibiotic treatment at 32 µg/mL for 60 minutes. This reduction is more significant than those at lower concentrations of the antibiotic. Hence, the concentration, i.e. 32 µg/mL, is determined as the minimum inhibitory concentration (MIC) of cephalexin.

Example 3

In the same manner as that of Example 1, a cefazolin solution at 2 µg/mL was prepared and used to act on *E. coli* ATCC 25922, w958, and BCRC 15501 for 120 minutes for the following dielectrophoretic testing. Among these cell lines, *E. coli* w958 from National Cheng Kung University Hospital in Taiwan is a drug-resistant bacterium isolated from clinical samples. The results are shown in FIGS. 4 (a) to (c).

Figure 4:
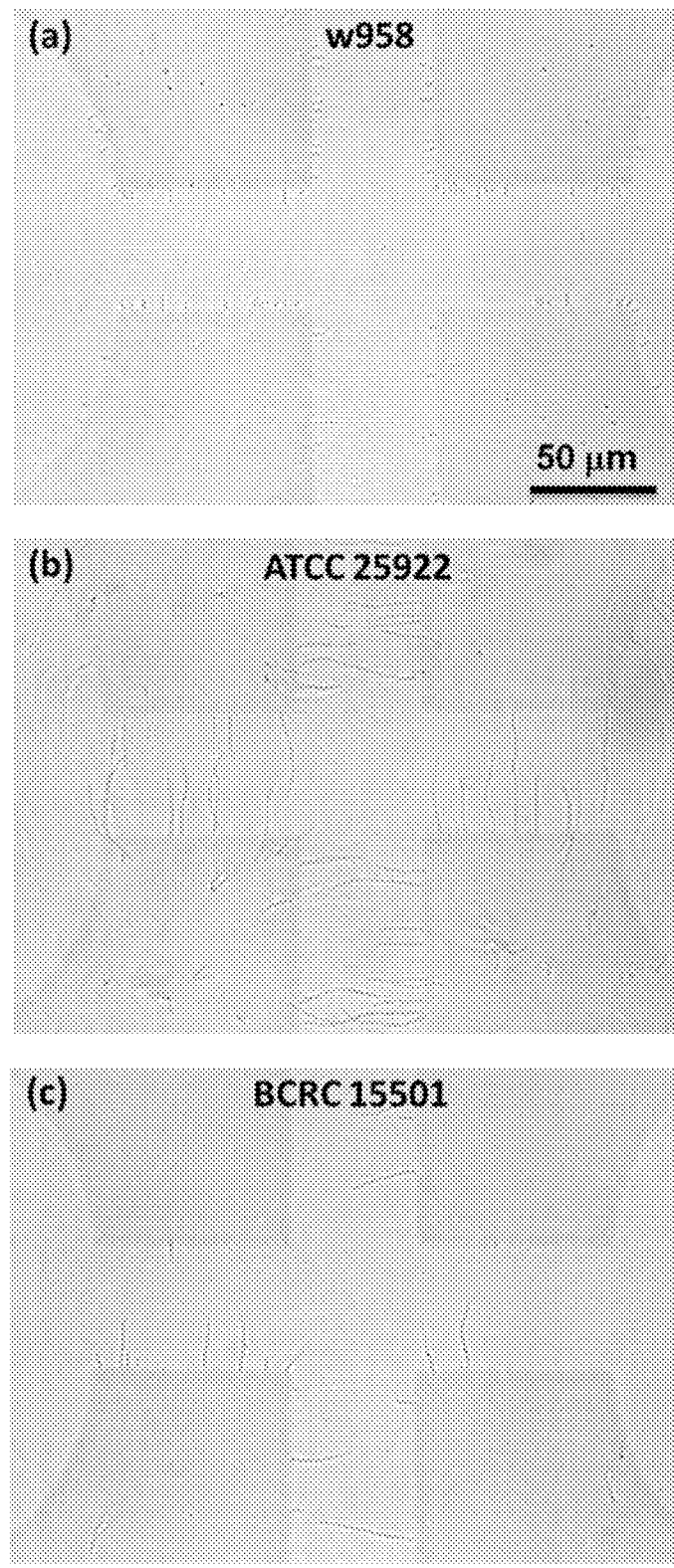
FIG. 4 shows microscopic photographs of a dielectrophoretic test in Example 3 of the present invention, wherein (a) shows test results of *Escherichia coli* w958, (b) shows test results of *Escherichia coli* ATCC 25922, and (c) shows test results of *Escherichia coli* BCRC 15501.

As shown in FIG. 4 (a), morphological cell elongation is unobvious in *E. coli* w958, and this indicates that *E. coli* w958 is resistant to cefazolin. Conversely, as shown in FIGS. 4 (b) and (c), obvious cell elongation occurs in *E. coli* ATCC 25922 and BCRC 15501 and this demonstrates that *E. coli* ATCC 25922 and BCRC 15501 can be inhibited by cefazolin and they both are not resistant to cefazolin.

Comparative Example 1

In order to confirm that the MIC determined in Example 2 of the present invention is not different from that determined in conventional methods, an agar dilution method was used to determine the MIC of cephalexin to *E. coli*. The result is shown in FIG. 5.

Figure 5:
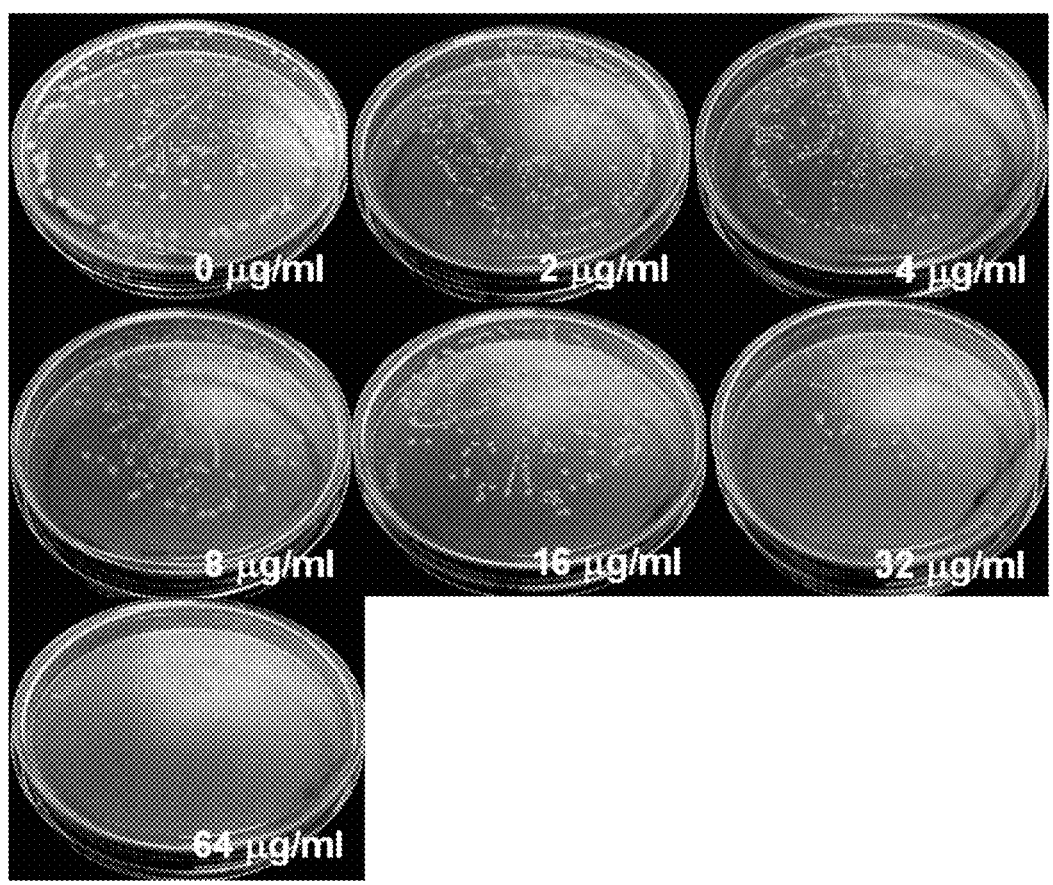
FIG. 5 shows culture plate photographs of a conventional agar dilution method in Comparative Example 1 of the present invention.

As shown in FIG. 5, MIC determined from the agar dilution method is between 32 µg/mL and 64 µg/mL. This result demonstrates that the MIC determined from Example 2 of the present invention is considerably correct.

Comparative Example 2

In order to confirm that the results from Example 3 of the present invention are not different from those from a conventional method, a broth dilution method was carried out on *E. coli* ATCC 25922, w958, and BCRC 15501 at 0 µg/mL, 0.5 µg/mL, 1 µg/mL, 2 µg/mL, 4 µg/mL, 8 µg/mL, 16 µg/mL of cefazolin. The results are shown in FIGS. 6 (a) to (c), wherein No denotes no bacteria.

Figure 6:
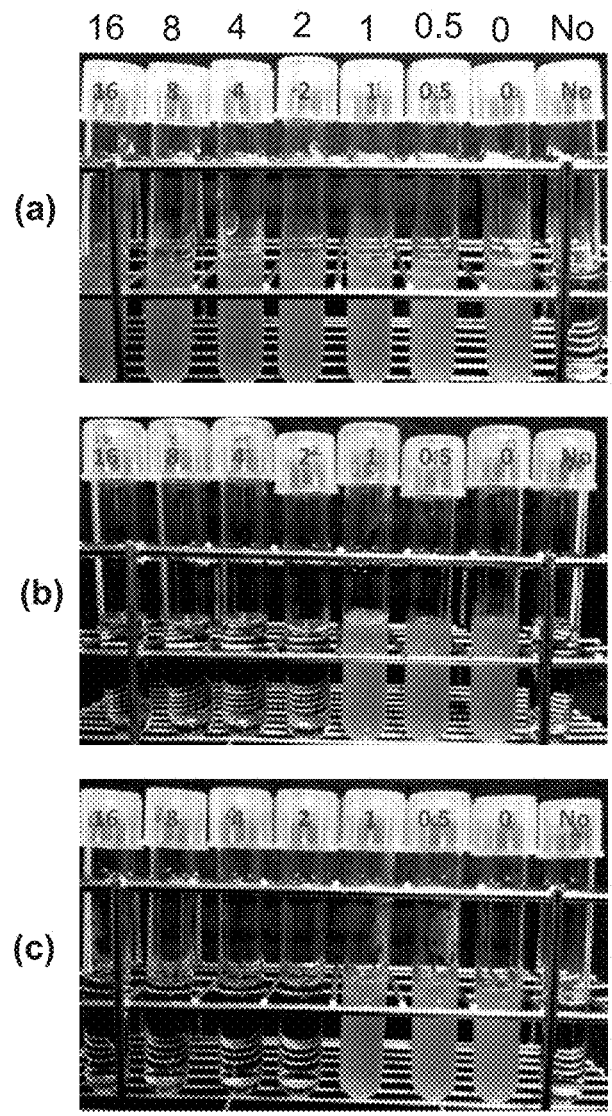
FIG. 6 shows culture tube photographs of a conventional broth dilution method in Comparative Example 2 of the present invention, wherein (a) shows test results of *Escherichia coli* w958, (b) shows test results of *Escherichia coli* ATCC 25922, and (c) shows test results of *Escherichia coli* BCRC 15501.

With reference to FIG. 6 (a), the result of *E. coli* w958, the upper figure shows that *E. coli* w958 is not inhibited even at 16 µg/mL of cefazolin. By contrast, with reference to FIGS. 6 (b) and (c), the results of *E. coli* ATCC 25922 and BCRC 15501, the upper figure shows that *E. coli* ATCC 25922 and BCRC 15501 are inhibited at 2 µg/mL of cefazolin. These results also demonstrate that the MIC determined from Example 3 of the present invention is considerably correct.

In conclusion, based on the phenomenon that dielectrophoresis is influenced by changes in bacterial activity, the present invention discovers that bacterial cell elongation accelerates under antibiotic treatment of increased concentrations, and thus different cell lengths induce different dielectrophoretic forces. Therefore, by supplying constant alternating current frequency, cell elongation becomes a basis for determining whether the bacteria are influenced by the antibiotic and whether they are drug resistant. In addition, by supplying specific alternating current frequency, the MIC of a certain antibiotic to a certain microbe can be determined according to changes in crossover frequency as well as cell elongation.

Although the inventors of the present invention combined dielectrophoresis and amikacin (an antibiotic inhibiting protein synthesis) to determine the MIC, the whole test consumed about 4 hours. By contrast, because the method of the present invention employs an antibiotic inhibiting cell wall synthesis as well as observation of cell elongation, the time of the whole test can be reduced to about 1 hour. Hence, the present invention is more efficient.

Although the present invention has been explained in relation to its preferred embodiment, it is to be understood that many other possible modifications and variations can be made without departing from the spirit and scope of the invention as hereinafter claimed.

What is claimed is:

1. A method of antibiotic susceptibility testing, comprising the following steps:
    (A) providing a test sample containing a microbe, wherein the microbe is a Gram-negative rod-shaped bacterium;
    (B) adding an antibiotic to the test sample, wherein the antibiotic is used to inhibit cell wall synthesis, and wherein the antibiotic is a β-lactam antibiotic;
    (C) executing dielectrophoresis to the test sample and observing morphologic changes of the microbe in the test sample; and
    (D) determining whether the microbe is resistant to the antibiotic according to the morphologic changes of the microbe.

2. The method of claim 1, wherein the Gram-negative rod-shaped bacterium is *Escherichia coli*, *Proteusbacillus vulgaris*, *Klebsiella pneumoniae*, or *Pseudomonas aeruginosa*.

3. The method of claim 1, wherein the antibiotic is selected from a group consisting of cephalosporins, monobactams, penicillins, carbapenems, and a combination thereof.

4. The method of claim 1, wherein in step (B), the antibiotic is present in the test sample for a predetermined period of time, and the predetermined period of time is 60-120 minutes.

5. A method for determining a minimum inhibitory concentration of an antibiotic, comprising the following steps:
    (A) providing a test sample containing a microbe, wherein the microbe is a Gram-negative rod-shaped bacterium;
    (B) adding an antibiotic with different concentrations to the test sample, wherein the antibiotic is used to inhibit cell wall synthesis, and wherein the antibiotic is a β-lactam antibiotic;
    (C) executing dielectrophoresis to the test sample and observing morphologic changes and crossover frequency changes of the microbe in the test sample; and (D) determining the minimum inhibitory concentration of the antibiotic according to the morphologic changes and the crossover frequency changes of the microbe.

6. The method of claim 5, wherein the Gram-negative rod-shaped bacterium is *Escherichia coli, Proteusbacillus vulgaris, Klebsiella pneumoniae,* or *Pseudomonas aeruginosa.*

7. The method of claim 5, wherein the antibiotic is selected from a group consisting of cephalosporins, monobactams, penicillins, carbapenems, and a combination thereof.

8. The method of claim 5, wherein in step (B), the antibiotic is present in the test sample for a predetermined period of time, and the predetermined period of time is 60-120 minutes.

\* \* \* \* \*